United States Patent [19]

Mock

[11] Plant 4,134

[45] Oct. 25, 1977

[54] CHRYSANTHEMUM

[76] Inventor: Norman Mock, 1363 Murphy Ave., San Jose, Calif. 95131

[21] Appl. No.: 735,156

[22] Filed: Oct. 26, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Boone, Schatzel, Hamrick & Knudsen

[57] ABSTRACT

A new variety of chrysanthemum plant originating as a seedling of the Red Rover (unpatented) and a miscellaneous yellow bloom, and characterized by its deeper red petal coloration, shorter petals, increased resistance to fading, smaller blooms and greater convexity of the individual petals.

1 Drawing Figure

1

BACKGROUND OF THE NEW PLANT

The present invention comprises a new and distinct cultivar of chrysanthemum plant which is a seedling of the cultivar commonly known in the United States as the Red Rover and a miscellaneous yellow bloom. The new cultivar was selected from the offspring of the aforementioned cross in October of 1973 in San Jose, Calif., and has been asexually reproduced by cuttings at the same location. The new cultivar has been found to retain its distinctive characteristics through successive propagations.

DESCRIPTION OF THE DRAWING

The accompanying drawing shows the unique characteristics of the new cultivar, the color being as nearly true as possible with color illustrations of this type. The upper photo shows the new cultivar by itself, and the comparison photo below shows the Mock Red Rover on the right and the parent cultivar Red Rover on the left.

DESCRIPTION OF THE NEW PLANT

The new cultivar is similar in many respects to the Red Rover, a well known unpatented commercial variety, and has the same characteristics as the Red Rover insofar as:

1. Response.
2. Height of plant.
3. Flower form.
4. Foliage size.
5. Foliage color.
6. Foliage shape.
7. Petal width.

The new cultivar is distinguished from the Red Rover by the following characteristics:

1. Petals are a deeper red color.

2 comparisons have been made in certain instances with the parent cultivar Red Rover.

Botanical classification: *Chrysanthemum morifolium.*

Bloom:

*Size.*—Medium.
*Fully expanded.*—4 inches. Red Rover: 4¼ inches.
*Borne.*—Singly on disbudded branches.
*Stems.*—Medium, normal.
*Form.*—Round, planar.
*Permanence.*—Hang on and dry.

| Color: | Mock Red Rover (New Cultivar) | Red Rover |
|---|---|---|
| Center of Flower | Green-Yellow 5.GY 6/10 | Yellow 2.5Y 8/14 |
| Base of petals | Yellow 10Y 8.5/8 | Yellow 10Y 8/8 |
| Inside of petals | Red F.5R 4/12 | Red-Yellow 2.5R 3/10 and 5Y 8.5/12 |
| Reverse of petals | Yellow-Red F.5Y 8.5/10 and F.5R 3/12 | Red-Yellow 2.5R 3/10 and 5Y 8.5/10 |
| Tonality from a distance | Red F.5R 3/10 | Red F.5R 3/10 |
| Discoloration | None | None |

Petals:

*Texture.*—Thin and soft.
*Appearance.*—Velvety/satiny.
*Arrangement.*—Imbricated.
*Persistence.*—Hang on and dry.
*Fragrance.*—Slight, typical chrysanthemum.

Reproductive organs:

*Stamen, anthers.*—Many, small.
*Pollen.*—5Y 8.5/14.
*Arrangement.*—Regular around styles.
*Styles.*—Columnar.
*Length.*—Long.
*Ovaries.*—Enclosed in calyx.

Plant:

*Form.*—Pillar.
*Growth.*—Medium, upright, branching.
*Height.*—Approximately 32 inches, depending on culture.
*Spread.*—None on single stem, 6 inches on pinched plant.

Foliage:

*Top side.*—Green 2.5G 3/4.
*Size.*—Medium.
*Quantity.*—Normal.
*Shape.*—Lanceolate.
*Texture.*—Glossy, smooth.
*Ribs and veins.*—Ordinary.
*Edge.*—Serrated.
*Serration.*—Single, small.

2. Petals are shorter in length.
3. Petals resist fading longer.
4. Greater number of stems per pinched plant.
5. Smaller blooms.
6. Greater convexity of individual petals.

The new cultivar is a short day response plant and, when grown in the vicinity of San Jose, Calif., has a response time of nine weeks. The bloom color is of a slightly deeper red during the winter growing period.

In the description which follows color references are made to the Munsell Book of Color, 1966 edition, and

*Underside.*—Green-yellow 7.5GY 4/4.
*Stipules.*—Short, smooth.

I claim:

1. A new and distinct cultivar of chrysanthemum characterized particularly in uniqueness when compared to the parent cultivar Red Rover by its deeper red petal coloration, shorter petals, increased resistance to fading, smaller blooms and greater convexity of the individual petals.

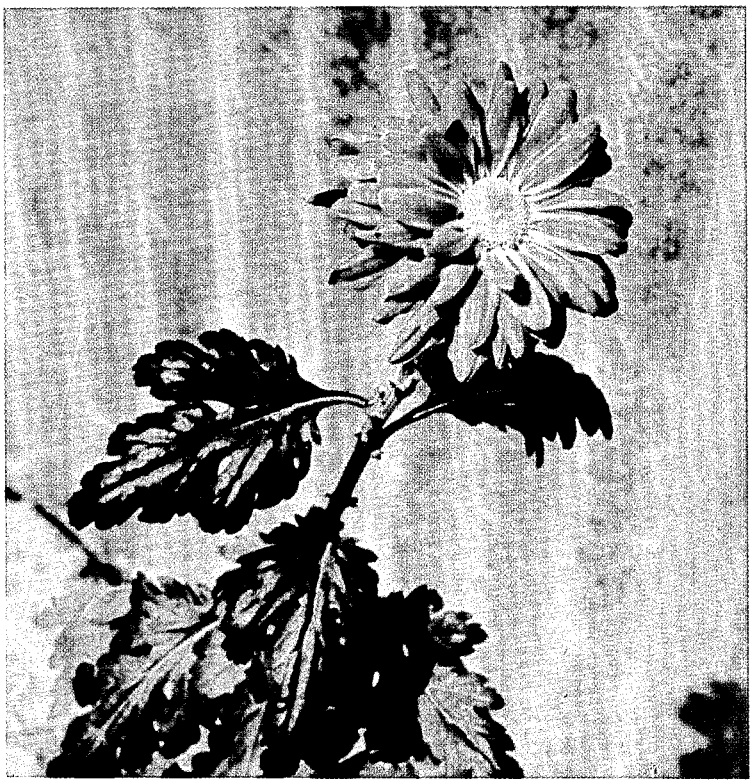
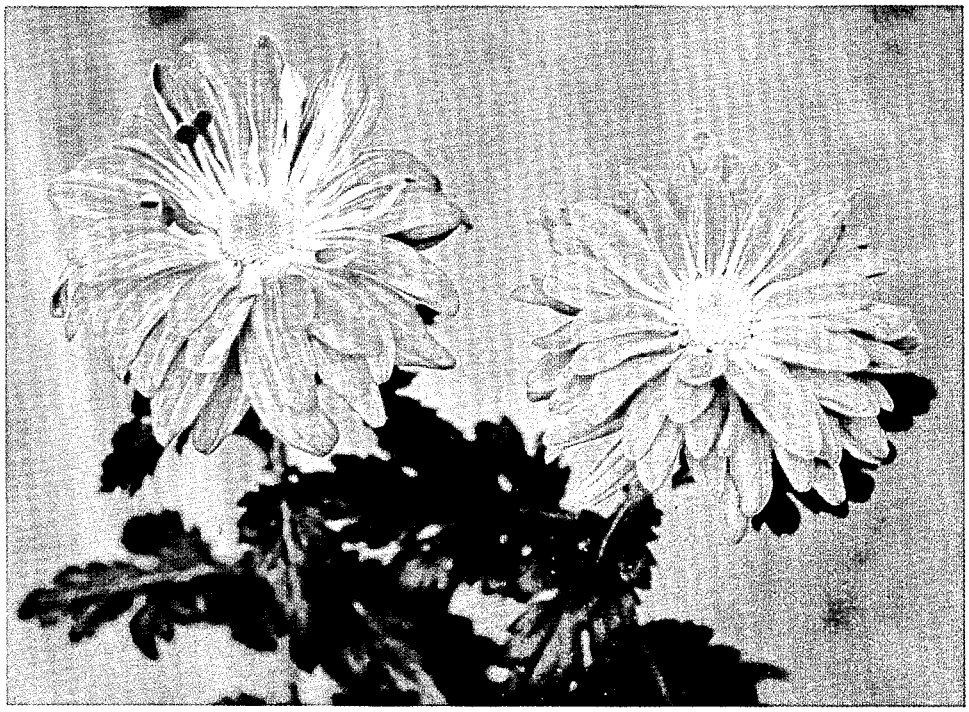

* * * * *